United States Patent

Hester, Jr.

[11] 3,995,043
[45] *Nov. 30, 1976

[54] COMPOSITION AND PROCESS

[75] Inventor: Jackson B. Hester, Jr., Galesburg, Mich.

[73] Assignee: The Upjohn Company, Kalamazoo, Mich.

[*] Notice: The portion of the term of this patent subsequent to May 22, 1990, has been disclaimed.

[22] Filed: Feb. 7, 1975

[21] Appl. No.: 547,804

Related U.S. Application Data

[63] Continuation-in-part of Ser. No. 469,394, May 13, 1974, abandoned.

[52] U.S. Cl. ............................ 424/263; 260/296 T
[51] Int. Cl.² .................................. C07D 487/04
[58] Field of Search ............... 260/296 T; 424/263

[56] References Cited
UNITED STATES PATENTS

3,734,922  5/1973  Hester ............................. 424/263

FOREIGN PATENTS OR APPLICATIONS

2,220,612  11/1972  Germany
2,220,615  11/1972  Germany

OTHER PUBLICATIONS

Chem. Abst. 78: 136353k (5–28–73).

*Primary Examiner*—Henry R. Jiles
*Assistant Examiner*—C. Jaisle
*Attorney, Agent, or Firm*—John T. Reynolds

[57] ABSTRACT

Pharmaceutical compositions comprising, in unit dosage form, from about 0.5 mg. to about 100 mg. of a compound of the formula

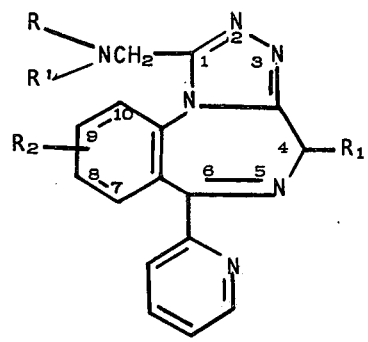

wherein R and R' are hydrogen, methyl or ethyl, $R_1$ is hydrogen or lower alkyl of 1 through 3 carbon atoms, $R_2$ is hydrogen, lower alkyl of 1 through 3 carbon atoms, fluorine, chlorine, bromine, nitro, trifluoromethyl or lower alkylthio of 1 through 3 carbon atoms, and the pharmacologically acceptable acid addition salts thereof, in association with a pharmaceutical carrier. The process is the administration of the above compositions to humans or animals at a dose of from about 0.01 mg./kg./day to about 2 mg./kg./day for anti-anxiety or anti-depressant effects.

6 Claims, No Drawings

COMPOSITION AND PROCESS

CROSS REFERENCE TO RELATED APPLICATIONS

This is a continuation-in-part of my U.S. Pat. application Ser. No. 469,394, filed May 13, 1974, and now abandoned.

BRIEF SUMMARY OF THE INVENTION

This invention is (1) a therapeutic composition for treating humans and animals comprising a benzodiazepine of Formula 1, above, and the pharmacologically acceptable acid addition salts thereof in combination with a pharmaceutical carrier and (2) a method for the treatment of conditions requiring anxiolytic (anti-anxiety) or anti-depressant medication with the aforesaid compositions.

The preferred compounds of Formula 1, above, employed in the compositions used in the method of treatment of this invention are embraced by the formula

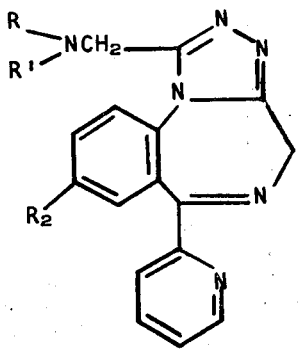

wherein R and R' are hydrogen or methyl, $R_2$ is hydrogen, fluorine, chlorine or bromine and the pharmacologically acceptable acid addition salts thereof.

DETAILED DESCRIPTION OF THE INVENTION

The following preparations and examples are illustrative of the manner of making and using the invention and set forth the best mode contemplated by the inventor of carrying out his invention, but are not to be construed as limiting the scope thereof, as obvious modifications and equivalents will be apparent to those skilled in the art, and the invention is therefore to be limited only by the scope of the appended claims.

The compounds of Formula I, above, can be prepared by the methods disclosed in U.S. Pat. No. 3,734,922 or German Offenlegungsschrift 2,244,488 (Derwent 18834U) in accordance with the sequence of formulae of Processes 1 or 2, respectively, set forth below.

wherein R, R', $R_1$ and $R_2$ have the same meaning as above.

Preparation 1

8-Bromo-1-[(dimethylamino)methyl]-6-(2-pyridyl)-4H-s-triazolo[4,3-a][1,4]benzodiazepine (I)

A stirred mixture of 3.32 g. (0.01 mole) of 7-bromo-1,3-dihydro-5-(2-pyridyl)-2H-1,4-benzodiazepine-2-thione (II) (prepared as in Example 1 of U.S. Pat. No. 3,734,922), 3.15 g. (0.03 mole) of (dimethylamino)acetic acid hydrazide and 1.50 ml. of n-butanol is refluxed for about 5.5 hours with a slow stream of nitrogen bubbling through the mixture. The mixture is cooled and then concentrated under vacuum, and the residue mixed with water and extracted with chloroform. The extract is washed with brine, dried with sodium sulfate and concentrated. This residue is chromatographed on a 150 g. column of silica gel with 3% methanol -97% chloroform. The resulting product is crystallized from ethyl acetate-Skellysolve B (hexanes) to give 1.9 g. of 8-bromo-1-[(dimethylamino)methyl]-6-(2-pyridyl)-4H-s-triazolo[4,3-a][1,4]benzodiazepine (I) melting at 162.5° to 164° C. and 0.174 g. melting at 163 to 164° C. The analytical sample melts at 163.5° to 165° C.

Anal. Calcd. for $C_{18}H_{17}BrN_6$: C, 54.42; H, 4.31; Br, 20.11; N, 21.15. Found: C, 54.38; H, 4.29; B, 20.03; N, 20.73.

Following the procedure of Preparation 1 but substituting another known representative 1,3-dihydro-5-(2-pyridyl)-2H-1,4-benzodiazepine-2-thione (II) starting material and reacting it with a known (dialkylamino)acetic acid hydrazide, such as (1) 7-bromo-1,3-dihydro-5-(2-pyridyl)-2H-1,4-benzodiazepine-2-thione (II) and aminoacetic acid hydrazide, (2) 7-bromo-1,3-dihydro-5-(2-pyridyl)-2H-1,4-benzodiazepine-2-thione (II) and (diethylamino)acetic acid hydrazide, (3) 7-bromo-1,3-dihydro-3-methyl-5-(2-pyridyl)-2H-1,4-benzodiazepine-2-thione (II) and (ethylmethylamino)acetic acid hydrazide, (4) 7-bromo-1,3-dihydro-3-propyl-5-(2-pyridyl)-2H-1,4-benzodiazepine-2-thione (II) and dimethylamino)acetic acid hydrazide, (5) 8-bromo-1,3-dihydro-5-(2-pyridyl)-2H-1,4-benzodiazepine-2-thione (II) and aminoacetic acid hydrazide, (6) 9-bromo-1,3-dihydro-5-(2-pyridyl)-2H-1,4-benzodiazepine-2-thione (II) and (diethylamino)acetic acid hydrazide, (7) 8-bromo-1,3-dihydro-3-ethyl-5-(2-pyridyl)-2H-1,4-benzodiazepine-2-thione (II) and (ethylmethylamino)acetic acid hydrazide,

PROCESS 1

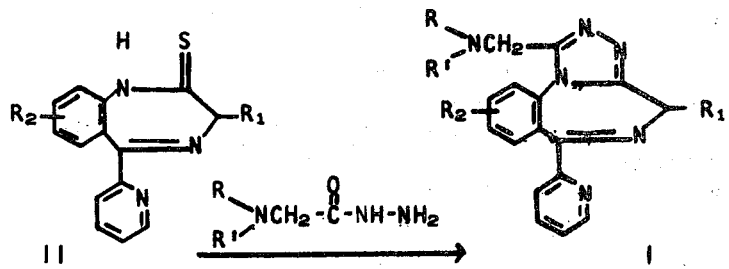

(8) 9-bromo-1,3-dihydro-3-methyl-5-(2-pyridyl)-2H-1,4-benzodiazepine-2-thione (II) and (dimethylamino)acetic acid hydrazide, (9) 1,3-dihydro-5-(2-pyridyl)-2H-1,4-benzodiazepine-2-thione (II) and (dimethylamino)acetic acid hydrazide,

(10) 7-chloro-1,3-dihydro-5-(2-pyridyl)-2H-1,4-benzodiazepine-2-thione (II) and aminoacetic acid hydrazide,

(11) 7-chloro-1,3-dihydro-5-(2-pyridyl)-2H-1,4-benzodiazepine-2-thione (II) and (dimethylamino)acetic acid hydrazide,

(12) 7-chloro-1,3-dihydro-3-ethyl-5-(2-pyridyl)2H-1,4-benzodiazepine-2-thione (II) and (ethylmethylamino)acetic acid hydrazide,

(13) 7-chloro-1,3-dihydro-3-methyl-5-(2-pyridyl)-2H-1,4-benzodiazepine-2-thione (II) and (diethylamino)acetic acid hydrazide,

(14) 8-chloro-1,3-dihydro-5-(2-pyridyl)-2H-1,4-benzodiazepine-2-thione (II) and aminoacetic acid hydrazide,

(15) 9-chloro-1,3-dihydro-5-(2-pyridyl)-2H-1,4-benzodiazepine-2-thione (II) and (diethylamino)acetic acid hydrazide, (16) 8-chloro-1,3-dihydro-3-propyl-5-(2-pyridyl)2H-1,4-benzodiazepine-2-thione (II) and (ethylmethylamino)acetic acid hydrazide,

(17) 9-chloro-1,3-dihydro-3-ethyl-5-(2-pyridyl)-2H-1,4-benzodiazepine-2-thione (II) and (dimethylamino)acetic acid anhydride,

(18) 1,3-dihydro-7-fluoro-5-(2-pyridyl)-2H-1,4-benzodiazepine-2-thione (II) and aminoacetic acid hydrazide,

(19) 1,3-dihydro-7-fluoro-5-(2-pyridyl)-2H-1,4-benzodiazepine-2-thione (II) and (dimethylamino)acetic acid hydrazide,

(20) 1,3-dihydro-7-fluoro-3-methyl-5-(2-pyridyl)-2H-1,4-benzodiazepine-2-thione (II) and (ethylmethylamino)acetic acid hydrazide,

(21) 1,3-dihydro-7-fluoro-3-propyl-5-(2-pyridyl)2H-1,4-benzodiazepine-2-thione (II) and (diethylamino)acetic acid hydrazide,

(22) 1,3-dihydro-8-fluoro-5-(2-pyridyl)-2H-1,4-benzodiazepine-2-thione (II) and aminoacetic acid hydrazide,

(23) 1,3-dihydro-9-fluoro-5-(2-pyridyl)-2H-1,4-benzodiazepine-2-thione (II) and (diethylamino)acetic acid hydrazide,

(24) 1,3-dihydro-8-fluoro-3-propyl-5-(2-pyridyl)2H-1,4-benzodiazepine-2-thione (II) and (ethylmethylamino)acetic acid hydrazide,

(25) 1,3-dihydro-9-fluoro-3-methyl-5-(2-pyridyl)2H-1,4-benzodiazepine-2-thione (II) and (dimethylamino) acetic acid hydrazide,

(26) 1,3-dihydro-7-methyl-5-(2-pyridyl)-2H-1,4-benzodiazepine-2-thione (II) and (dimethylamino)acetic acid hydrazide,

(27) 1,3-dihydro-8-ethyl-3-methyl-5-(2-pyridyl)-2H-1,4-benzodiazepine-2-thione (II) and (diethylamino)acetic acid hydrazide, and the like, yields, respectively, (1) 1-aminomethyl-8-bromo-6-(2-pyridyl)-4H-s-triazolo[4,3-a][1,4]-benzodiazepine (I), (2) 8-bromo-1-[(diethylamino)methyl]-6-(2-pyridyl)4H-s-triazolo[4,3-a][1,4]benzodiazepine (I)

(3) 8-bromo-1-[(ethylmethylamino)methyl]-4-methyl-6-(2pyridyl)-4H-s-triazolo[4,3-a][1,4]benzodiazepine (I), (4) 8-bromo-1-[(dimethylamino)methyl]-4-propyl-6-(2-pyridyl)-4H-s-triazolo[4,3-a][1,4]benzodiazepine (I), (5) 1-aminomethyl-9-bromo-6-(2-pyridyl)-4H-s-triazolo[4,3-a][1,4]benzodiazepine (I), (6) 10-bromo-1-[(diethylamino)methyl]-6-(2-pyridyl)4H-s-triazolo[4,3-a][1,4]benzodiazepine (I), (7) 9-bromo-4-ethyl-1-[(ethylmethylamino)methyl]6-(2-pyridyl)-4H-s-triazolo[4,3-a][1,4]benzodiazepine (I), (8) 10-bromo-1[(dimethylamino)methyl]-4-methyl-6-(2-pyridyl)-4H-s-triazolo[4,3-a][1,4]benzodiazepine (I), (9) 1-[(dimethylamino)methyl]-6-(2-pyridyl)-4H-s-triazolo[4,3-a][1,4-benzodiazepine (I),

(10) 1-aminomethyl-8-chloro-6-(2-pyridyl)-4H-s-triazolo[4,3-a][1,4]-benzodiazepine (I),

(11) 8-chloro-1-[(dimethylamino)methyl]-6-(2-pyridyl)4H-s-triazolo[4,3-a][1,4]benzodiazepine (I),

(12) 8-chloro-4-ethyl-1-[(ethylmethylamino)methyl]6-(2-pyridyl)-4H-s-triazolo[4,3-a][1,4-benzodiazepine (I), (13) 8-chloro-1-[(diethylamino)methyl]-4-methyl-6-(2-pyridyl)-4H-s-triazolo[4,3-a][1,4]benzodiazepine (I),

(14) 1-aminomethyl-9-chloro-6-(2-pyridyl)-4H-s-triazolo[4,3-a][1,4]benzodiazepine (I),

(15) 10-chloro-1-[(diethylamino)methyl]-6-(2-pyridyl)4H-s-triazolo[4,3-a][1,4]benzodiazepine (I),

(16) 9-chloro-1-[(ethylmethyl)amino]-4-propyl-6-(2-pyridyl)-4H-s-triazolo[4,3-a][1,4]benzodiazepine (I),

(17) 10-chloro-1-[(diethylamino)methyl]-4-ethyl-6(2-pyridyl)-4H-s-triazolo[4,3-a][1,4]benzodiazepine (I),

(18) 1-aminomethyl-8-fluoro-6-(2-pyridyl)-4H-s-triazolo[4,3-a][1,4]benzodiazepine (I),

(19) 1-[(dimethylamino)methyl]-8-fluoro-6-(2-pyridyl)-4H-s-triazolo[4,3-a][1,4]benzodiazepine (I),

(20) 1-[(ethylmethylamino)methyl]-8-fluoro-4-methyl-6-(2-pyridyl)-4H-s-triazolo[4,3-a][1,4]benzodiazepine (I),

(21) 1-[diethylamino)methyl]-8-fluoro-4-propyl-6-(2-pyridyl)-4H-s-triazolo[4,3-a][1,4]benzodiazepine (I),

(22) 1-aminomethyl-9-fluoro-6-(2-pyridyl)-4H-s-triazolo[4,3-a][1,4]-benzodiazepine (I),

(23) 1-[(diethylamino)methyl]-10-fluoro-6-(2-pyridyl)-4H-s-triazolo[4,3-a][1,4]benzodiazepine (I),

(24) 1-[(ethylmethylamino)methyl]-9-fluoro-4-propyl-6-(2-pyridyl)-4H-s-triazolo[4,3-a][1,4]benzodiazepine (I),

(25) 1-[(dimethylamino)methyl]-10-fluoro-4-methyl-6-(2-pyridyl)-4H-s-triazolo[4,3-a][1,4]benzodiazepine (I),

(26) 1-[(dimethylamino)methyl]-8-methyl-6-(2-pyridyl)-4H-s-triazolo[4,3-a][1,4]benzodiazepine (I),

(27) 1-[(diethylamino)methyl]-9-ethyl-4-methyl-6-(2-pyridyl)-4H-s-triazolo[4,3-a][1,4]benzodiazepine (I), and the like.

PROCESS 2

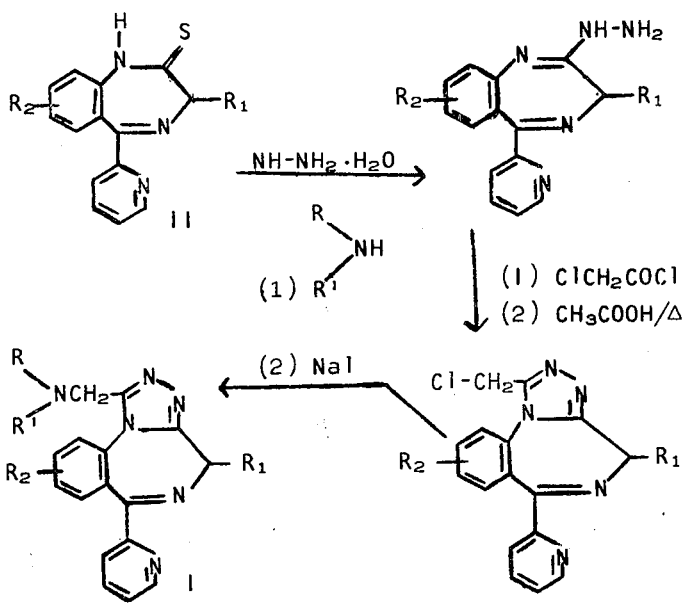

wherein R, R', $R_1$ and $R_2$ have the same meaning as above.

Preparation 2

7-bromo-5-(2-pyridyl)-3H-1,4-benzodiazepin-2-yl hydrazine

A stirred mixture of 16.61 g. (0.05 mole) of 7-bromo-1,3-dihydro-5-(2-pyridyl)-2H-1,4-benzodiazepine-2thione (II) and 400 ml. of methanol is treated with 7.51 ml. of hydrazine hydrate and allowed to remain at ambient temperature for about 18 hours. A slow stream of nitrogen is bubbled through the mixture during this period. The resulting precipitate is collected by filtration, washed with methanol and dried to give 14.25 g. of 7-bromo-5-(2-pyridyl)-3H-1,4-benzodiazepine-2-yl hydrazine with a melting point of 218°–228° C. with decomposition.

Preparation 3

8-bromo-1-(chloromethyl)-6-(2-pyridyl)-4H-s-triazolo[4,3-a][1,4-benzodiazepine 15 g. of 7-bromo-5-(2-pyridyl)-3H-1,4-benzodiazepin-2-yl hydrazine (obtained as in Preparation 2) is slowly added to 150 ml. of acetic acid with external cooling. A solution of 6 g. of chloroacetyl chloride in 75 ml. of acetic acid is then added during about ten minutes, the solution is stirred at room temperature for about 1.5 hours and 4 g. of sodium acetate added with additional stirring for about 30 minutes, the mixture then being refluxed for about 3.25 hours. This mixture is cooled, poured into ice water and concentrated to a small volume, then diluted with water, neutralized with sodium bicarbonate and extracted with chloroform. The extract is dried over anhydrous magnesium sulfate, concentrated and the residue chromatographed on 1 kg. column of silica gel with 1% methanol — 99% chloroform. The product obtained from the column is crystallized from ethyl acetate to give pure 8-bromo-1-(chloromethyl)-6-(2-pyridyl)-4H-s-triazolo-[4,3-a][1,4]benzodiazepine.

Following the procedures of Preparations 2 and 3, but substituting another known representative, 1,3-dihydro-5-(2-pyridyl)-2H-1,4-benzodiazepine-2-thione for the starting material of Preparation 2, such as (1) 7-bromo-1,3-dihydro-3-ethyl-5-(2-pyridyl)-2H-1,4-benzodiazepine-2-thione, (2) 8-bromo-1,3-dihydro-5-(2-pyridyl)-2H-1,4-benzodiazepine-2-thione, (3) 9-bromo-1,3-dihydro-5-(2-pyridyl)-2H-1,4-benzodiazepine-2-thione, (4) 7-chloro-1,3-dihydro-5-(2-pyridyl)-2H-1,4-benzodiazepine-2-thione, (5) 7-methylthio-1,3-dihydro-5-(2-pyridyl)-2H-1,4-benzodiazepine-2-thione, (6) 9-chloro-1,3-dihydro-5-(2-pyridyl)-2H-1,4-benzodiazepine-2-thione, (7) 1,3-dihydro-7-fluoro-5-(2-pyridyl)-2H-1,4-benzodiazepine-2-thione, (8) 1,3-dihydro-7-trifluoromethyl-5-(2-pyridyl)-2H-1,4-benzodiazepine-2-thione, (9) 1,3-dihydro-7-nitro-5-(2-pyridyl)-2H-1,4-benzodiazepine-2-thione, and the like, yields a compound akin to the one produced in Preparation 3, respectively, (1) 8-bromo-1-(chloromethyl)-4-ethyl-6-(2-pyridyl)-4H-s-triazolo[4,3-a][1,4]benzodiazepine, (2) 9-bromo-1-(chloromethyl)-6-(2-pyridyl)-4H-s-triazolo[4,3-a][1,4]benzodiazepine, (3) 10-bromo-1-(chloromethyl)-6-(2-pyridyl)-4H-s-triazolo[4,3-a][1,4]benzodiazepine, (4) 8-chloro-1-(chloromethyl)-6-(2-pyridyl)-4H-s-triazolo[4,3-a][1,4]benzodiazepine, (5) 8-methylthio-1-(chloromethyl)-6-(2-pyridyl)-4H-s-triazolo[4,3-a][1,4]benzodiazepine, (6) 10-chloro-1-(chloromethyl)-6-(2-pyridyl)-4H-s-triazolo[4,3-a][1,4]-benzodiazepines, (7) 1-(chloromethyl)-8-fluoro-6-(2-pyridyl)-4H-s-triazolo[4,3-a][1,4]benzodiazepine, (8) 1-(chloromethyl)-8-trifluoromethyl-6-(2-pyridyl)-4H-s-triazolo[4,3-a][1,4]benzodiazepine, (9) 1-chloromethyl)-8-nitro-6-(2-pyridyl)-4H-s-triazolo[4,3-a][1,4]benzodiazepine, and the like.

Preparation 4

8-bromo-1-[(diethylamino)methyl]-6-(2-pyridyl)-4H-s-triazolo[4,3-a][1,4]benzodiazepine (I)

To a solution of 1 ml. of diethylamine in 5 ml. of dry dimethylformamide, 350 mg. of 8-bromo-1-(chloromethyl)-6-(2-pyridyl)-4H-s-triazolo[4,3-a][1,4]benzodiazepine (obtained as in Preparation 3) is added and the mixture stirred under nitrogen at room temperature for about 4.5 hours. To the mixture, 50 mg. of sodium iodide is added and stirring is continued at room temperature for about 18 hours and then heated at about 100 to about 110° C. for about an additional 6 hours. It is then poured into ice water and extracted with chloroform. The extract is washed with water, dried over anhydrous potasssium carbonate and concentrated under vacuum. The residue is crystallized from ethyl acetate: Skellysolve B to give pure 8-bromo-1-[(diethylamino)methyl]-6-(2-pyridyl)-4H-s-triazolo[4,3-a][1,4]benzodiazepine (I).

Following the procedure of Preparation 4 but substituting another 1-(chloromethyl)-6-(2-pyridyl)-4H-s-triazolo[4,3-a][1,4]benzodiazepine as starting material and another amine for diethylamine, such as (1) 7-bromo-1-(chloromethyl)-6-(2-pyridyl)-4H-s-triazolo[4,3-a][1,4]benzodiazepine and ammonia, (2) 8-bromo-1-(chloromethyl)-6-(2-pyridyl)-4H-s-triazolo[4,3-a][1,4]benzodiazepine and dimethylamine, (3) 9-bromo-1-(chloromethyl)-4-methyl-6-(2-pyridyl)-4H-s-triazolo[4,3-a][1,4]benzodiazepine and diethylamine, (4) 10-bromo-1-(chloromethyl)-6-(2-pyridyl)-4H-s-triazolo[4,3-a][1,4]benzodiazepine and ethylmethylamine, (5) 7-chloro-1-(chloromethyl)-6-(2-pyridyl)-4H-s-triazolo[4,3-a][1,4]benzodiazepine and dimethylamine, (6) 8-chloro-1-(chloromethyl)-4-propyl-6-(2-pyridyl)-4H-s-triazolo[4,3-a][1,4]benzodiazepine and diethylamine, (7) 8-methylthio-1-(chloromethyl)-6-(2-pyridyl)-4H-s-triazolo[4,3-a][1,4]benzodiazepine and ammonia, (8) 1-(chloromethyl)-8-nitro-6-(2-pyridyl)-4H-s-triazolo[4,3-a][1,4]benzodiazepine and dimethylamine, (9) 1-(chloromethyl)-8-fluoro-6-(2-pyridyl)-4H-s-triazolo[4,3-a][1,4]benzodiazepine and diethylamine,

(10) 1-(chloromethyl)-8-trifluoromethyl-6-(2-pyridyl)-4H-s-triazolo[4,3-a][1,4]benzodiazepine and ethylmethylamine, and the like, yields, respectively, (1) 1-aminomethyl-7-bromo-6-(2-pyridyl)-4H-s-triazolo[4,3-a][1,4]benzodiazepine (I), (2) 8-bromo-1-[(dimethylamino)methyl]-6-(2-pyridyl)-4H-s-triazolo[4,3-a][1,4]benzodiazepine (I), (3) 9-bromo-1-[(dimethylamino)methyl]-4-methyl-6-(2-pyridyl)-4H-s-triazolo[4,3-a][1,4]benzodiazepine (I), (4) 10-bromo-1-[(ethylmethylamino)methyl]-6-(2-pyridyl)-4H-s-triazolo[4,3-a][1,4]benzodiazepine (I), (5) 7-chloro-1-[(dimethylamino)methyl]-6-(2-pyridyl)4H-s-triazolo[4,3-a][1,4]benzodiazepine (I), (6) 8-chloro-1-[(diethylamino)methyl]-4-propyl-6-(2-pyridyl)-4H-s-triazolo[4,3-a][1,4]benzodiazepine (I), (7) 1-aminomethyl-8-methylthio-6-(2-pyridyl)-4H-s-triazolo[4,3-a][1,4]benzodiazepine (I), (8) 1-[(dimethylamino)methyl]-8-nitro-6-(2-pyridyl)-4H-s-triazolo[4,3-a][1,4]benzodiazepine (I), (9) 1-[(diethylamino)methyl]-8-fluoro-6-(2-pyridyl)-4H-s-triazolo[4,3-a][1,4]benzodiazepine (I),

(10) 1-[(ethylmethylamino)methyl]-8-trifluoromethyl-6-(2-pyridyl)-4H-s-triazolo[4,3-a][1,4]benzodiazepine (I),
and the like.

The compounds of the Formula I show both anti-depressive and anti-anxiety activities. They can be used when prepared in unit dosage forms, in association with a pharmaceutical carrier for treatment of both depression or anxiety as well as mixed states of anxiety and depression such as occur in certain neurosis, sometimes referred to as the anxiety-depression syndrome.

The compositions of the present invention are presented for systemic administration to humans and animals in unit dosage form and can be administered orally, parenterally, and rectally.

For oral administration either solid or fluid unit dosage forms can be prepared. For preparing solid compositions such as tablets, the compound of Formula 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For rectal administration a compound of the Formula I in the form of a suppository is preferred and is prepared by compounding with a solid which melts at body temperature, e.g., cocoa butter or a solid which is miscible in body fluids, e.g., polyethylene glycol. Similarly, solutions which are adapted for use as retention enemas can be prepared.

The term unit dosage form as used in the specification and claims refers to physically discrete units suitable as unitary dosages for human subjects and animals, each unit containing a predetermined quantity of active material calculated to produce a sleep in association with the requirred pharmaceutical diluent, carrier, or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans and animals, as disclosed in detail in this specification, these being features of the present invention. Examples of suitable dosage forms in accord with this invention are tablets, capsules, pills, suppositories, powder packets, granules, wafers, cachets, teaspoonfuls, tablespoonfuls, dropperfuls, ampuls, vials, segregated multiples of any of the foregoing, and other forms as herein described.

The dosage of the compound for treatment depends on route of administration, the age, weight, and condition of the patient. The dosage to be administered is calculated on the basis of from about 0.01 to about 2 mg./kg. weight of subject/day.

The compound is compounded with a suitable pharmaceutical carrier in unit dosage form for convenient and effective administration. In the preferred embodiments of this invention, the dosage units contain the compound in: 0.5, 1, 10, 25, 50, and 100 mg. amounts for systemic treatment; and 0.5% to 5% w/v for parenteral treatment.

EXAMPLE 1

A lot of 10,000 tablets, each containing 0.5 mg. of 8-bromo-1-[(dimethylamino)methyl]-6-(2-pyridyl)-4H-s-triazolo[4,3-a][1,4]benzodiazepine is prepared from the following types and amounts of ingredients:

| | |
|---|---|
| 8-bromo-1-[(dimethylamino)-methyl]-6-(2-pyridyl)-4H-s-triazolo[4,3-a]-[1,4]benzodiazepine | 5 gm. |
| Dicalcium phosphate | 1,500 gm. |
| Methylcellulose, U.S.P. (15 cps.) | 60 gm. |
| Talc | 150 gm. |
| Corn Starch | 200 gm. |
| Calcium stearate | 12 gm. |

The benzodiazepine and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful for treatment of anxiety and depression at a dose of 2-4 tablets a day.

EXAMPLE 2

One thousand two-piece hard gelatin capsules, each containing 1 mg. of 8-bromo-1-[(dimethylamino)methyl]-6-(2-pyridyl)-4H-s-triazolo[4,3-a][1,4]benzodiazepine are prepared from the following types and amounts of ingredients:

| | |
|---|---|
| 8-bromo-1-[(dimethylamino)-methyl]-6-(2-pyridyl)-4H-s-triazolo[4,3-a][1,4]benzodiazepine | 1 gm. |
| Talc | 25 gm. |
| Lactose | 125 gm. |
| Magnesium stearate | 2.5 gm. |
| Starch | 30 gm. |

The ingredients are mixed well and filled into capsules of the proper size.

Capsules so prepared are useful for treatment of anxiety and depression at a dose of 1 capsule four times a day.

EXAMPLE 3

One thousand tablets for sublingual use are prepared from the following ingredients:

| | |
|---|---|
| 8-bromo-1-[(dimethylamino)-methyl]-6-(2-pyridyl)-4H-s-triazolo[4,3-a][1,4]benzodiazepine | 10 gm. |
| Polyethylene glycol, 4,000 powdered | 150 gm. |
| Polyethylene glycol, 6,000 powdered | 75 gm. |

The ingredients are mixed well and compressed into sublingual-type tablets weighing 235 mg.

These tablets placed under the tongue are useful in the rapid induction of treatment for anxiety and depression at a dose of 1 tablet 4 times a day.

EXAMPLE 4

Soft gelatin capsules for oral use, each containing 10 mg. of 8-bromo-1-[(dimethylamino)methyl]-6-(2-pyridyl)-4H-s-triazolo[4,3-a][1,4]benzodiazepine are prepared by first dispersing the micronized compound in corn oil to render the material capsulatable and then encapsulating in the usual manner.

One capsule taken daily is useful for anxiety and depression.

EXAMPLE 5

One thousand tablets, each containing 25 mg. of 8-bromo-1-[(dimethylamino)methyl]-6-(2-pyridyl)-4H-s-triazolo[4,3-a][1,4]benzodiazepine are made from the following types and amounts of ingredients:

| | |
|---|---|
| 8-bromo-1-[(dimethylamino)-methyl]-6-(2-pyridyl)-4H-s-triazolo[4,3-a][1,4]benzodiazepine | 25 gm. |
| Lactose | 355 gm. |
| Microcrystalline cellulose NF | 100 gm. |
| Starch | 16 gm. |
| Magnesium stearate powder | 4 gm. |

The ingredients are screened and blended together and pressed into 500 mg. tablets.

The tablets are useful for treating anxiety and depression at a dose of 1 tablet 3 times a day.

EXAMPLE 6

A sterile preparation suitable for intramuscular injection and containing 10 mg. of 8-bromo-1-[(dimethylamino)methyl]-6-(2-pyridyl)-4H-s-triazolo[4,3-a][1,4]benzodiazepine in each milliliter is prepared from the following ingredients:

| | |
|---|---|
| 8-bromo-1-[(dimethylamino)methyl]-6-(2-pyridyl)-4H-s-triazolo[4,3-a][1,4]benzodiazepine | 10 gm. |
| Benzyl benzoate | 2 ml. |
| Methylparaben | 1.5 gm. |
| Propylparaben | 0.5 gm. |
| Cottonseed oil q.s. | 1,000 ml. |

One milliliter of this sterile preparation is injected for treatment of neurotic depression.

EXAMPLE 7

One thousand tablets, each containing 50 mg. of 8-bromo-1-[(dimethylamino)methyl]-6-(2-pyridyl)-4H-s-triazolo[4,3-a][1,4]benzodiazepine methanesulfonate are made from the following types and amounts of ingredients:

| | |
|---|---|
| 8-bromo-1-[(dimethylamino)methyl]-6-(2-pyridyl)-4H-s-triazolo[4,3-a][1,4]benzodiazepine methanesulfonate | 50 gm. |
| Lactose | 330 gm. |
| Microcrystalline cellulose NF | 100 gm. |
| Starch | 16 gm. |
| Magnesium stearate powder | 4 gm. |

The ingredients are screened and blended together and pressed into 500 mg. tablets.

The tablets are useful for treating neurotic depression at a dose of 1 tablet 3 times a day.

EXAMPLE 8

One thousand two-piece hard gelatin capsules, each containing 100 mg. of 8-bromo-1-[(dimethylamino)methyl]-6-(2-pyridyl)-4H-s-triazolo[4,3-a][1,4]benzodiazepine are prepared from the following types and amounts of ingredients:

| | |
|---|---|
| 8-bromo-1-[(dimethylamino)methyl]-6-(2-pyridyl)-4H-s-triazolo[4,3-a][1,4]benzodiazepine | 100 gm. |
| Starch | 30 gm. |
| Talc | 25 gm. |
| Magnesium stearate | 2.5 gm. |
| Lactose | 50 gm. |

The ingredients are mixed well and filled into capsules of the proper size.

Capsules so prepared are useful to reduce anxiety and depression in adults at a dose of one to two capsules daily.

EXAMPLE 9

A sterile aqueous solution for parenteral administration containing 25 mg. of 8-bromo-1-[(dimethylamino)methyl]-6-(2-pyridyl)-4H-s-triazolo[4,3-a][1,4]benzodiazepine methanesulfonate in each 1 ml., is prepared from the following types and amounts of ingredients:

| | |
|---|---|
| 8-bromo-1-[(dimethylamino)methyl]-6-(2-pyridyl)-4H-s-triazolo[4,3-a][1,4]benzodiazepine methanesulfonate | 25 gm. |
| Water for injection q.s. | 1000 ml. |

The active ingredient is dissolved in the water for injection and the solution sterilized by filtration. The sterile solution is filled into 1 ml. sterile vials and sealed.

The composition is useful for treating anxiety and depression at a dose of 1 to 2 ml. daily.

EXAMPLE 10

One thousand ml. of an elixir, containing 100 mg. of 8-bromo-1-[(dimethylamino)methyl]-6-(2-pyridyl)-4H-s-triazolo[4,3-a][1,4]benzodiazepine methanesulfonate in each 5 ml. is prepared from the following types and amounts of ingredients:

| | |
|---|---|
| 8-bromo-1-[(dimethylamino)methyl]-6-(2-pyridyl)-4H-s-triazolo[4,3-a][1,4]benzodiazepine methanesulfonate | 20 gm. |
| Citric acid | 0.1 gm. |
| F.D.C. Red No. 1 | 0.04 gm. |
| Saccharin | 0.1 gm. |
| Sucrose | 200.0 gm. |
| Oil of spearmint | 0.1 gm. |
| Oil of Wintergreen | 0.1 gm. |
| Polysorbate 80 U.S.P. | 1.0 gm. |
| Ethanol 95% | 200.0 ml. |
| Glycerin | 150.0 ml. |
| Water q.s. | 1,000.0 ml. |

The sugar is dissolved in 450 ml. of water and the citric acid, color and the 8-bromo-1-[(dimethylamino)methyl]-6-(2-pyridyl)-4H-s-triazolo[4,3-a][1,4]benzodiazepine methanesulfonate added thereto. The saccharin is added to the mixture of alcohol and glycerin and stirred until dissolved. The flavors are mixed with the polysorbate 80 and added to the alcohol-glycerin solution followed by the addition of the sugar solution and sufficient water to make 1,000 ml.

The elixir is useful in the treatment of anxiety and depression at a dose of 1 to 2 teaspoons a day.

EXAMPLE 11

Following the procedures of preceding Examples 1 through 8, unit dosage forms are similarly prepared substituting an equal amount each of 8-chloro-1-[aminomethyl]-6-(2-pyridyl)-4H-s-triazolo[4,3-a][1,4]benzodiazepine, 8-chloro-1-[(methylamino)methyl]-6-(2-pyridyl)-4H-s-triazolo[4,3-a][1,4]benzodiazepine, 8-chloro-1-[(ethylmethylamino)methyl]-6-(2-pyridyl)-4H-s-triazolo[4,3-a][1,4]benzodiazepine, 8-chloro-1-[(diethylamino)methyl]-6-(2-pyridyl)-4H-s-triazolo[4,3-a][1,4]benzodiazepine, 8-chloro-1-[(dimethylamino)methyl]-6-(2-pyridyl)-4H-s-triazolo[4,3-a][1,4]benzodiazepine, 8-bromo-1-[(methylamino)methyl]-6-(2-pyridyl)-4H-s-triazolo[4,3-a][1,4]benzodiazepine, 8-trifluoromethyl-1-[(amino)methyl]-6-(2-pyridyl)-4H-s-triazolo[4,3-a][1,4]benzodiazepine, 8-bromo-1-[(diethylamino)methyl]-6-(2-pyridyl)-4H-s-triazolo[4,3-a][1,4]benzodiazepine, 8-bromo-1-[(ethylmethylamino)methyl]-

6-(2-pyridyl)-4H-s-triazolo[4,3-a][1,4]benzodiazepine, 8-fluoro-1-[(dimethylamino)methyl]-6-(2-pyridyl)-4H-s-triazolo[4,3-a][1,4]benzodiazepine, and 8-fluoro-1-(aminomethyl)-6-(2-pyridyl)-4H-s-triazolo[4,3-a][1,4]benzodiazepine for 8-bromo-1-[(dimethylamino)methyl]-6-(2-pyridyl)-4H-s-triazolo[4,3-a][1,4]benzodiazepine.

I claim:

1. A pharmaceutical composition for treating anxiety or depression comprising, in unit dosage form, from about 0.5 mg. to about 100 mg. of a compound of the formula

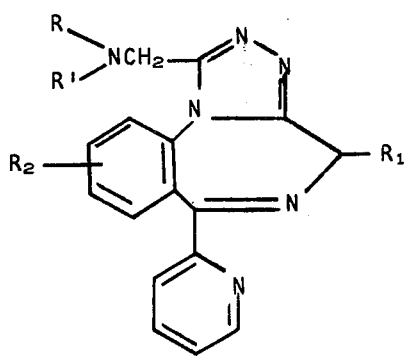

wherein R and R' are hydrogen, methyl or ethyl, $R_1$ is hydrogen or lower alkyl of 1 through 3 carbon atoms, $R_2$ is hydrogen, lower alkyl of 1 through 3 carbon atoms, fluorine, chlorine, bromine, nitro, trifluoromethyl or lower alkylthio of 1 through 3 carbon atoms, or a pharmacologically acceptable acid addition salt thereof, in association with a pharmaceutical carrier.

2. The composition of claim 1 wherein R and R' are methyl, $R_1$ is hydrogen and $R_2$ is 8-bromo, namely, 8-1-[(dimethylamino)methyl]-6-(2-pyridyl)-4H-s-triazolo[4,3-a][1,4]benzodiazepine.

3. A process for treating anxiety and depression comprising the administration to a human or animal subject in need of such treatment, an effective amount of a compound of the formula

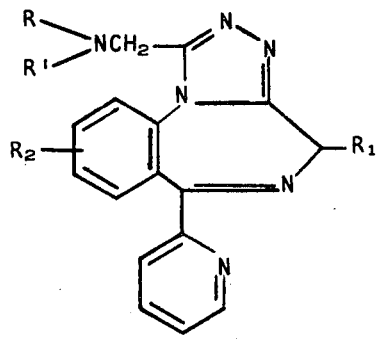

wherein R and R' are hydrogen, methyl or ethyl, $R_1$ is hydrogen or lower alkyl of 1 through 3 carbon atoms, $R_2$ is hydrogen, lower alkyl of 1 through 3 carbon atoms, fluorine, chlorine, bromine, nitro, trifluoromethyl or lower alkylthio of 1 through 3 carbon atoms, or a pharmacologically acceptable acid addition salt thereof, in association with a pharmaceutical carrier.

4. A process in accordance with claim 3 wherein from about 0.01 mg./kg./day to about 2 mg./kg./day of the compound is administered.

5. The process of claim 4 wherein the compound administered is 8-bromo-1-[(dimethylamino)methyl]-6-(2-pyridyl)-4H-s-triazolo[4,3-a][1,4]benzodiazepine.

6. 8-Bromo-1-[(dimethylamino)methyl]-6-(2-pyridyl)-4H-s-triazolo[4,3-a][1,4]benzodiazepine.

* * * * *